(12) United States Patent
Valster et al.

(10) Patent No.: US 11,103,665 B2
(45) Date of Patent: Aug. 31, 2021

(54) RESPIRATORY APPARATUS AND METHOD OF OPERATING THE RESPIRATORY APPARATUS

(71) Applicant: KONINKLIJKE PHILIPS N.V., Eindhoven (NL)

(72) Inventors: Susanne Maaike Valster, Valkenswaard (NL); Raymond Van Ee, Geldrop (NL); Kiran Hamilton J. Dellimore, Utrecht (NL); Mark Thomas Johnson, Arendonk (BE); Ron Martinus Laurentius Van Lieshout, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 427 days.

(21) Appl. No.: 15/805,259

(22) Filed: Nov. 7, 2017

(65) Prior Publication Data

US 2018/0126107 A1 May 10, 2018

(30) Foreign Application Priority Data

Nov. 9, 2016 (EP) .................................... 16197958

(51) Int. Cl.
*A61M 16/06* (2006.01)
*A61N 1/04* (2006.01)
(Continued)

(52) U.S. Cl.
CPC ....... *A61M 16/0633* (2014.02); *A61B 5/4812* (2013.01); *A61B 5/4836* (2013.01); *A61M 16/0003* (2014.02); *A61M 16/0605* (2014.02); *A61M 16/0683* (2013.01); *A61M 21/02* (2013.01); *A61N 1/0452* (2013.01); *A61N 1/36003* (2013.01); *A61N 1/36014* (2013.01);
(Continued)

(58) Field of Classification Search
None
See application file for complete search history.

(56) References Cited

U.S. PATENT DOCUMENTS

| 3,279,468 A | 10/1966 | Le Vine |
| 6,524,225 B1 * | 2/2003 | Arias ................... A63B 23/032 482/11 |

(Continued)

FOREIGN PATENT DOCUMENTS

| JP | 2003339884 A | 12/2003 |
| WO | 2010048261 A1 | 4/2010 |
| WO | 2012068613 A1 | 5/2012 |

OTHER PUBLICATIONS

Kraft, T. et al., "Grin and Bear It: The Influence of Manipulated Facial Expression on the Stress Response", Association for Psychological Science, Sep. 19, 2011.
(Continued)

*Primary Examiner* — Lynsey C Eiseman
*Assistant Examiner* — Amanda L. Steinberg (57) ABSTRACT

There is provided a respiratory apparatus. The respiratory apparatus comprises a respiratory interface configured to aid a user in respiration and an attachment configured to hold the respiratory interface in position on the face of the user. The respiratory apparatus also comprises at least one electrode configured to provide electrical stimulation to one or more facial muscles of the user.

16 Claims, 2 Drawing Sheets

(51) Int. Cl.
| | |
|---|---|
| A61N 1/36 | (2006.01) |
| A61B 5/00 | (2006.01) |
| A61M 21/02 | (2006.01) |
| A61M 16/00 | (2006.01) |
| A62B 9/00 | (2006.01) |
| A62B 18/08 | (2006.01) |
| A61M 21/00 | (2006.01) |

(52) U.S. Cl.
CPC .......... *A61N 1/36031* (2017.08); *A62B 9/006* (2013.01); *A62B 18/084* (2013.01); *A61M 16/0688* (2014.02); *A61M 21/00* (2013.01); *A61M 2016/0027* (2013.01); *A61M 2021/0072* (2013.01); *A61M 2205/05* (2013.01); *A61M 2205/054* (2013.01); *A61M 2205/3303* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2230/04* (2013.01); *A61M 2230/10* (2013.01); *A61M 2230/14* (2013.01); *A61M 2230/18* (2013.01); *A61M 2230/60* (2013.01); *A61M 2230/63* (2013.01)

(56) References Cited

U.S. PATENT DOCUMENTS

| | | | |
|---|---|---|---|
| 7,575,005 | B2 | 8/2009 | Mumford et al. |
| 8,000,812 | B2 | 8/2011 | Paolizzi et al. |
| 9,259,576 | B2 | 2/2016 | Popovic et al. |
| 9,372,533 | B1 | 6/2016 | Agrama |
| 9,687,619 | B2 * | 6/2017 | Stuebiger .......... A61M 16/0683 |
| 2002/0161416 | A1 | 10/2002 | Huang |
| 2005/0268916 | A1 * | 12/2005 | Mumford .............. A61M 16/06 128/207.13 |
| 2009/0038617 | A1 * | 2/2009 | Berthon-Jones ..... A61B 5/0205 128/204.23 |
| 2011/0295083 | A1 * | 12/2011 | Doelling ................ A61B 5/103 600/301 |

OTHER PUBLICATIONS

Ekman, P. et al., "The Duchenne Smile: Emotional Expression and Brain Physiology II", Journal of Personality and Social Psychology, 1990, vol. 58, No. 342-353.

Kim, K. et al., "Application of isometric load on a facial muscle—The zygomaticus major", Clinical Biomechanics, vol. 24, 2009, pp. 606-612.

Stalberg, S., "SFEMG: Stimulation—Orbicularis Oculi", YouTube video, Apr. 16, 2012, https://www.youtube.com/watch?v=P04eeaLB4Wg.

Selvan, V., "Single-fiber EMG: A review", Annals of Indian Academy of Neurology, Jan.-Mar. 2011, 14(1): 64-67.

Trojan, D. et al., "Stimulation frequency-dependent neuromuscular junction transmission defects in patients with prior poliomyelitis", Journal of the Neurological Sciences, 118, 1993, pp. 150-157.

Kall, R., "Emotional Self Regulation and Facial Expression Muscle Measurement and Training", 1989, https://www.futurehealth.org/populum/pagesimple.php?f=Emotional-Self-Regulation-And-Facial-Exp-101.html.

Kolen, A.F. et al., "Electromyography experiments towards new muscle stimulation strategies", Philips Technical Note, Mar. 2009.

Li C. et al., "Excitability Characteristics of the A- and C-Fibers in a Peripheral Nerve", Experimental Neurology, 50, 67-79 (1976).

"Procedural memory", Wikipedia article, last edited Oct. 7, 2017, https://en.wikipedia.org/wiki/Procedural_memory.

Born, J. et al., "Sleep to Remember", Department of Neuroendocrinology, University of Lubeck, Germany, The Neuroscientist, vol. 12, No. 5, 2006, pp. 410-424.

Datta, S., "Avoidance Task Training Potentiates Phasic Pontine-Wave Density in the Rat: A Mechanism for Sleep-Dependent Plasticity", The Journal of Neuroscience, Nov. 15, 2000, 20(22): 8607-8613.

Tuhn, T., "Tens unit to the face", YouTube Video, Published on Nov. 24, 2011, https://www.youtube.com/watch?v=Jd0yiz-VKKw.

M. Johnson, M. Martinson, Philips Tens Machine PulseRelief Wireless Electro Pulse Therapy, 2007, https://www.amazon.co.uk/Philips-Machine-PulseRelief-Wireless-Electro/dp/B00YGR5616.

Kawamoto, K. et al., "Actigraphic Detection of REM Sleep Based on Respiratory Rate Estimation", Journal of Medical and Bioengineering, vol. 2, No. 1, Mar. 2013, pp. 20-25.

Yaso, M. et al., "Detection of REM sleep by heart rate", Proceedings of the First International Workshop on Kansei, Jan. 1, 2006.

O'Brien, B. et al., "StretchSense", https://stretchsense.com/, 2012.

Sady, C. et al., "Automatic sleep staging from ventilator signals in non-invasive ventilation", Computers in Biology and Medicine, 2013, pp. 833-839.

Martin, L. et al., "Non-invasive positive pressure therapy: CPAP, BiPAP, ASV", May 3, 2011, http://www.lakesidepress.com/CPAP/CPAP.htm.

\* cited by examiner

RESPIRATORY APPARATUS AND METHOD OF OPERATING THE RESPIRATORY APPARATUS

CROSS-REFERENCE TO PRIOR APPLICATIONS

This application claims the benefit of European Patent Application No. 16197958.8, filed on 9 Nov. 2016. This application is hereby incorporated by reference herein.

TECHNICAL FIELD OF THE INVENTION

The invention relates to a respiratory apparatus and a method of operating the respiratory apparatus.

BACKGROUND TO THE INVENTION

A respiratory apparatus often needs to be worn by a user with a respiratory condition. U.S. Pat. No. 7,575,005 B2 discloses an example of such a respiratory apparatus, which is used for treating sleep apnoea. The need for a user to wear a respiratory apparatus can negatively affect the mood and stress level of the user, particularly since the user already has health issues, and can thus have a detrimental impact of their wellbeing.

In order to counteract a negative mood and decrease stress, people are often encouraged by therapists to make use of their facial muscles to smile or laugh since this is known to lift the mood and reduce stress. It can also have other health benefits such as reducing blood pressure. However, people are reluctant to participate in this type of therapy since it is time consuming and can make the person feel uncomfortable. It would thus be useful to aid a user of a respiratory apparatus to improve their wellbeing in some other way, which achieves the same positive health benefits but without action from the user themselves to achieve those benefits.

Another issue with existing respiratory apparatus is that often the respiratory interface of the respiratory apparatus that is worn on the face of the user can leak. It would thus also be useful to improve the air tightness of the respiratory interface on the face of the user.

Therefore, there is a need for an improved respiratory apparatus, which can overcome the existing problems mentioned above.

SUMMARY OF THE INVENTION

As noted above, it would be valuable to have an improved respiratory apparatus to overcome the existing problems.

Therefore, according to a first aspect of the invention, there is provided a respiratory apparatus. The respiratory apparatus comprises a respiratory interface configured to aid a user in respiration, an attachment configured to hold the respiratory interface in position on the face of the user, and at least one electrode configured to provide electrical stimulation to one or more facial muscles of the user.

In some embodiments, the attachment may comprise at least one strap or at least one adhesive member. In some embodiments, the attachment may comprise the at least one electrode.

In some embodiments, the respiratory apparatus may comprise at least one pair of electrodes and the at least one pair of electrodes may be configured to provide electrical stimulation to corresponding muscles on each side of the face of the user. In some embodiments, the one or more facial muscles of the user may comprise any one or more of a zygomaticus major muscle of the user and an orbicularis oculi muscle of the user.

In some embodiments, the respiratory apparatus may further comprise at least one sleep stage sensor configured to acquire a signal indicative of a sleep stage of the user. In some embodiments, the at least one sleep stage sensor may comprise any one or more of a physiological characteristic sensor, an eye movement sensor, and an activity sensor.

In some embodiments, the at least one electrode may be controllable to provide electrical stimulation to the one or more facial muscles of the user when the acquired signal is indicative of the user sleeping. In some embodiments, the at least one electrode may be controllable to provide electrical stimulation to the one or more facial muscles of the user when the acquired signal is indicative of the user being in a rapid eye movement sleep stage. In some embodiments, an intensity of the electrical stimulation may be based on the acquired signal indicative of a sleep stage of the user.

In some embodiments, the respiratory apparatus may further comprise at least one muscle contraction sensor configured to detect one or more muscle contractions in the face of the user. In some embodiments, an intensity of the electrical stimulation may be based on the one or more muscle contractions detected in the face of the user.

In some embodiments, the respiratory apparatus may further comprise an air pressure sensor configured to monitor an air pressure within the respiratory interface, wherein, if the monitored air pressure is indicative of a leak in the respiratory interface on the face of the user, the at least one electrode may be controllable to adjust the electrical stimulation provided to the one or more facial muscles of the user.

In some embodiments, the respiratory apparatus may be a continuous positive airway pressure apparatus.

According to a second aspect of the invention, there is provided a method of operating a respiratory apparatus as described above. The method comprises controlling the at least one electrode to provide the electrical stimulation to the one or more facial muscles of the user.

According to a third aspect of the invention, there is provided a computer program product comprising a computer readable medium, the computer readable medium having computer readable code embodied therein, the computer readable code being configured such that, on execution by a suitable computer or processor, the computer or processor is caused to perform the method described above.

According to the aspects and embodiments described above, the existing limitations described earlier are addressed. In particular, the air tightness of the respiratory interface on the face of the user can be improved. Specifically, by stimulating facial muscles of the user via at least one electrode, the topology of the face of the user can be changed. The face of the user can be manipulated in such way that an air seal between the respiratory interface and the face of the user is improved. The improved air seal can reduce the amount of leaks in the respiratory interface and can even make the respiratory interface leak tight. In this way, the primary function of the respiratory apparatus can be improved.

Also, through the stimulation of facial muscles via at least one electrode, the user is subconsciously guided to store the use of the stimulated facial muscles in their procedural memory. This makes it easier for the user to use the stimulated facial muscles, which can subconsciously encourage the user to use these facial muscles. It can also be useful in improving the mood and emotional state of the user, particularly where the facial muscles used for smiling are stimulated (such as the zygomaticus major and/or orbicularis oculi muscles).

In this way, the wellbeing of the user of the respiratory apparatus can be improved such as by improving the mood of the user, reducing stress, and thus improving the general health of the user. This can be particularly beneficial to users of respiratory apparatus that suffer from health issues such as sleep apnoea, depression, high blood pressure, and/or respiratory conditions. Moreover, the benefits provided by the respiratory apparatus according to the above aspect and embodiments can be achieved without interfering with the daily life of the user.

There is therefore provided an improved respiratory apparatus, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF EMBODIMENTS

As noted above, the invention provides an improved respiratory apparatus, which overcomes the existing problems.

The improved respiratory apparatus is intended to be worn by a user (for example, a subject, a patient, or any other user). Thus, the respiratory apparatus comprises an attachment that is configured to hold the respiratory interface in position on the face of the user. For example, the attachment can comprise at least one strap, at least one adhesive member, or any other attachment suitable to hold the respiratory interface in position on the face of the user. The attachment may be an existing attachment of the respiratory apparatus or a dedicated attachment added to the respiratory apparatus. In some embodiments, the respiratory apparatus can be a respiratory apparatus intended to be worn while the user is sleeping (for example, placed on the face of the user prior to the user going to bed). In other words, the respiratory apparatus may be a respiratory sleep apparatus.

The respiratory apparatus comprises a respiratory interface. The respiratory interface is configured to aid a user in respiration. Specifically, the respiratory interface is configured to provide a connection to the airway of the user. In some embodiments, the respiratory interface may comprise a respiratory mask. The respiratory interface (or the respiratory mask) may be configured to cover the mouth of the user, the nose of the user, both the mouth and the nose of the user, or the entire face of the user, to aid the user in respiration. The respiratory interface may be configured to aid the user in respiration by supplying a flow of gas (e.g. air) to the user. In some embodiments, the respiratory interface may comprise a tube via which the flow of gas can be delivered to the user. The respiratory apparatus may further comprise a pump configured to deliver the flow of gas to the user.

The respiratory apparatus can be any type of respiratory apparatus. For example, the respiratory apparatus may be a positive airway pressure PAP apparatus such as a continuous positive airway pressure (CPAP) apparatus, an automatic positive airway pressure (APAP) apparatus, a variable/bi-level positive airway pressure (VPAP/BPAP) apparatus, or any other PAP apparatus, an adaptive servo ventilation (ASV) apparatus, a proportional-assist ventilation (PAV) apparatus, a tracheal intubation apparatus, or any other type of respiratory apparatus.

The respiratory apparatus also comprises at least one electrode configured to provide electrical stimulation to one or more facial muscles of the user. The at least one electrode can be positioned in the respiratory apparatus at any location suitable to provide electrical stimulation to the one or more facial muscles of the user. In some embodiments, the attachment can comprise at least one electrode.

In embodiments where the attachment comprises at least one strap, the at least one strap can comprise at least one electrode. For example, an electrode may be integrated in at least one strap (such as integrated in the material of at least one strap). Thus, at least one strap of the respiratory apparatus can be configured to cover at least a part of the face of the user at which one or more of the facial muscles are located. In embodiments in which the attachment comprises at least one adhesive member, the at least one adhesive member can comprise at least one electrode. For example, an electrode may be integrated in at least one adhesive member (such as integrated in the material of at least one adhesive member). Thus, at least one adhesive member of the respiratory apparatus can be configured to cover at least a part of the face of the user at which one or more of the facial muscles are located. Although examples have been provided for the location of the at least one electrode, it will be understood that any other part of the respiratory apparatus can, alternatively or in addition, comprise at least one electrode.

In some embodiments, the respiratory apparatus may comprise at least one pair of electrodes. The at least one pair of electrodes can be configured to provide electrical stimulation to corresponding muscles on each side of the face of the user.

The one or more facial muscles of the user can comprise any facial muscles of the user. In some embodiments, for example, the one or more facial muscles may comprise any facial muscle used in forming a facial expression indicative of a positive mood or emotional state of the user (such as one or more facial muscles used when the user smiles or laughs). For example, the one or more facial muscles may comprise any one or more of a zygomaticus major muscle of the user (such as the zygomaticus major muscle on the right side of the face of the user, the zygomaticus major muscle on the left side of the face of the user, or both of the zygomaticus major muscles), an orbicularis oculi muscle of the user (such as the orbicularis oculi muscle on the right side of the face of the user, the orbicularis oculi muscle on the left side of the face of the user, or both of the orbicularis oculi muscles), or both a zygomaticus major muscle of the user (which may be one or both of the zygomaticus major muscles) and an orbicularis oculi muscle of the user (which may be one or both of the orbicularis oculi muscles).

The zygomaticus major muscle of the user is located in the cheek area, extending down to the mouth of the user. Thus, at least one electrode may be positioned at a location on the cheek on one or both sides of the face of the user to provide electrical stimulation to one or both of the zygomaticus major muscles. In an embodiment in which the attachment comprises at least one electrode, the attachment comprising at least one electrode for providing electrical stimulation to the zygomaticus major muscle may be configured to lie over the cheek of the user (such as at the lower part of the cheek toward to the outer corner of the mouth). The orbicularis oculi muscle of the user is located around the eyes. Thus, at least one electrode may be positioned at a location between the eye and the ear of the user on one or both sides of the face of the user to provide electrical stimulation to one or both of the orbicularis oculi muscles. In an embodiment in which the attachment comprises at least one electrode, the attachment comprising at least one electrode for providing electrical stimulation to the orbicularis oculi muscle may be configured to lie between the eye and the ear of the user.

Although examples have been provided for the number of electrodes, for the arrangement and location of the electrodes, and for the facial muscles, it will be understood that the respiratory apparatus can comprise any number of electrodes, which can be arranged and located at any location suitable to provide electrical stimulation to one or more facial muscles of the user, and can be configured to provide electrical stimulation to any facial muscle of the user.

In some embodiments, the respiratory apparatus may further comprise at least one sleep stage sensor configured to acquire a signal indicative of a sleep stage of the user. For example, the attachment (such as at least one strap, at least one adhesive member, or any other attachment) of the respiratory apparatus may comprise at least one sleep stage sensor. Alternatively or in addition, at least one sleep stage sensor configured to acquire a signal indicative of a sleep stage of the user may be external to (i.e. separate to or remote from) the respiratory apparatus. For example, one or more sleep stage sensors may be comprised in another device such as a mobile device (e.g. a smart phone, a tablet, or a device dedicated for the purpose of acquiring a signal indicative of a sleep stage of the user), in the bed of the user, or at any other location external to the respiratory apparatus at which the sleep stage sensor can acquire a signal indicative of a sleep stage of the user.

The signal indicative of a sleep stage of the user can be any signal that can be processed to differentiate between at least two sleep stages of the user. For example, the signal indicative of a sleep stage of the user may be any signal that can be processed to at least differentiate between a sleeping stage of the user and a non-sleeping stage of the user or to at least differentiate between a rapid eye movement (REM) sleep stage of the user and a non-rapid eye movement (non-REM) sleep stage of the user. The at least one sleep stage sensor can comprise a physiological characteristic (or vital sign) sensor, an eye movement sensor, an activity sensor, or any other sleep stage sensor, or any combination of sleep stage sensors suitable to acquire a signal indicative of a sleep stage of the user.

A physiological characteristic (or vital sign) sensor may comprise any sensor suitable to acquire one or more physiological characteristics (or vital signs) of the user that can be indicative of a sleep stage of the user. For example, a physiological characteristic sensor may comprise any one or more of a heart rate sensor, a brain activity sensor, a respiratory sensor, or any other physiological characteristic sensor, or any combination of physiological characteristic sensors.

A heart rate sensor may comprise any sensor suitable to acquire heart rate data from the user, which can be indicative of a sleep stage of the user. Examples of a heart rate sensor include, but are not limited to, an electrocardiogram (ECG) sensor, a photoplethysmography (PPG) sensor, a phonocardiography (PCG) sensor, an acceleration sensor, a Doppler radar sensor, or any other heart rate sensor, or any combination of heart rate sensors. A brain activity sensor may comprise any sensor suitable to acquire brain activity data from the user, which can be indicative of a sleep stage of the user. Examples of a brain activity sensor include, but are not limited to, an electroencephalography (EEG) sensor (which may comprise an array of electrodes such as an array of six electrodes or any other number of electrodes), a near infrared (NIR) sensor, or any other brain activity sensor, or any combination of brain activity sensors. A respiratory sensor may comprise any sensor suitable to acquire respiratory data (such as ventilation signals) from the user, which can be indicative of a sleep stage of the user. Examples of a respiratory sensor include, but are not limited to, the respiratory device itself, an electrocardiogram (ECG) sensor, an impedance sensor, an acceleration sensor, a photoplethysmography (PPG) sensor, a Doppler radar sensor, or any other respiratory sensor, or any combination of respiratory sensor.

An eye movement sensor may comprise any sensor suitable to acquire eye movement data from the user that can be indicative of a sleep stage of the user. More specifically, an eye movement sensor may be any sensor that can directly detect or establish eye movement (such as rapid eye movement and non-rapid eye movement) that can be used to identify a sleep stage of the user. For example, an eye movement sensor may comprise any one or more of a visual sensor (such as a camera), an optical sensor, an acceleration sensor, an electrooculography (EOG) sensor, or any other eye movement sensor, or any combination of eye movement sensors.

An activity (or motion or inertial) sensor may comprise any sensor suitable to acquire activity (or motion or inertial) data on the user that can be indicative of a sleep stage of the user. For example, an activity sensor may comprise any one or more of an accelerometer, a gyroscope, a magnetometer, a visual sensor (such as a camera), a pressure sensor, a Doppler radar sensor, or any other activity sensor, or any combination of activity sensors.

In some embodiments, the respiratory apparatus may further comprise at least one muscle contraction sensor configured to detect one or more muscle contractions in the face of the user. The at least one muscle contraction sensor may be located at any location of the respiratory apparatus, which allows the at least one sensor to detect one or more muscle contractions in the face of the user. In some embodiments, for example, the attachment (such as at least one strap, at least one adhesive member, or any other attachment) of the respiratory apparatus may comprise one or more muscle contraction sensors. In these embodiments, the one or more muscle contraction sensors of the attachment may be a stretch sensor suitable to detect (or measure) stretching of the attachment. The one or more muscle contraction sensors can, for example, comprise any one or more of a fabric stretch sensor, a silicone stretch sensor, an inductance plethysmography sensor, an acceleration sensor, an electromyography sensor, a strain gauge, or any other sensor suitable for detecting one or more muscle contractions, or any combination of those sensors. In some embodiments, the at least one muscle contraction sensor may be located at the same location as at least one electrode. In other embodiments, the at least one muscle contraction sensor may be located as a different location to the at least one electrode. For example, the location at which a facial muscle contracts may not necessarily be the location at which at least one electrode provides electrical stimulation to that facial muscle.

Although examples have been provided for the type of sleep stage sensor, the type of muscle contraction sensor, and for the location of those sensors, it will be understood that any sleep stage sensor or any combination of sleep stage sensors suitable to acquire a signal indicative of a sleep stage of the user can be used, any muscle contraction sensor or any combination of muscle contraction sensors suitable to detect muscle contractions in the face of the user can be used, and that those sensors may be located at any location that is suitable for the intended purpose of those sensors.

In some embodiments, the respiratory apparatus may comprise a communications interface (or circuitry) for enabling the respiratory apparatus to communicate with any sensors, units, interfaces, and devices that are internal or external to the respiratory apparatus. The communications interface may communicate with any sensors, units, interfaces, and devices wirelessly or via a wired connection.

In some embodiments, the respiratory apparatus can comprise a control unit (such as a central processing unit CPU). Alternatively, in some embodiments, the control unit may be external to (i.e. separate to or remote from) the respiratory apparatus. For example, the control unit may be comprised in another device. In the embodiments in which the control unit is external to the respiratory apparatus, the control unit may communicate with the respiratory apparatus either wirelessly or via a wired connection using the communications interface. Thus, according to some embodiments, there is provided a system comprising the respiratory apparatus described herein and a control unit configured to control operation of the respiratory apparatus in the manner described herein.

In some embodiments, the control unit may be configured to control the flow of gas (e.g. air) supplied to the user in accordance with the usual operation of a respiratory interface. Alternatively or in addition, in some embodiments, the control unit may be configured to control the at least one electrode to provide the electrical stimulation to the one or more facial muscles of the user. Alternatively or in addition, in some embodiments, the control unit may be configured to process signals, measurements, information or data acquired from sensors (such as any sleep stage sensors and/or muscle contraction sensors) of the respiratory apparatus or that are external to the respiratory apparatus and to control the at least one electrode appropriately.

The control unit can comprise one or more processors, processing units, multi-core processors or modules that are configured or programmed to control operation of the respiratory apparatus in the manner described herein. In particular implementations, the control unit can comprise a plurality of software and/or hardware modules that are each configured to perform, or are for performing, individual or multiple steps of the method according to embodiments of the invention.

In some embodiments, the respiratory apparatus may also comprise a memory configured to store program code that can be executed by the control unit to perform the method described herein. The memory can also be used to store information, data, signals and measurements acquired or made by the control unit, any sensors of the respiratory apparatus, and/or any sensors external to the apparatus. In embodiments in which the control unit is external to the respiratory apparatus, the memory may also be external to the respiratory apparatus. For example, the memory may be comprised in another device (such as a device comprising the control unit).

In some embodiments, the apparatus may also comprise a user interface. Alternatively or in addition, at least one user interface may be external to (i.e. separate to or remote from) the apparatus. For example, a user interface may be part of another device (such as a device comprising the control unit). The user interface may be configured to receive a user input. For example, a user interface may allow the user of the respiratory apparatus to manually enter instructions (such as a preferred setting for the electrical stimulation provided by the at least one electrode of the respiratory apparatus). The control unit may be configured to acquire the user input from the user interface for use in controlling the respiratory apparatus. Thus, the user interface may be any user interface that enables a user of the respiratory apparatus to provide a user input, interact with and/or control the respiratory apparatus. For example, the user interface may comprise one or more switches, one or more buttons, a keypad, a keyboard, a touch screen or an application (for example, on a mobile device such as a tablet or smartphone), one or more microphones, or any other user interface component, or combination of user interface components for receiving a user input.

In some embodiments, the respiratory apparatus may also comprise a battery or other power supply for powering the respiratory apparatus. For example, the respiratory interface, the attachment (such as at least one strap, at least one adhesive member, or any other attachment), or any other part of the respiratory apparatus may comprise a battery or other power supply for powering the respiratory apparatus. Alternatively or in addition, the respiratory apparatus may comprise means for connecting the respiratory apparatus to a mains power supply. The battery or power supply may, for example, power the at least one electrode of the respiratory apparatus. In embodiments in which the respiratory apparatus comprises one or more sensors, the battery or power supply may also power the sensors. Similarly, in embodiments in which the respiratory apparatus comprises a control unit, the battery or power supply may also power the control unit. The battery or power supply may be electrically connected to the at least one electrode, any sensors, and any control unit of the respiratory apparatus via one or more electrical wires.

Figure 1:
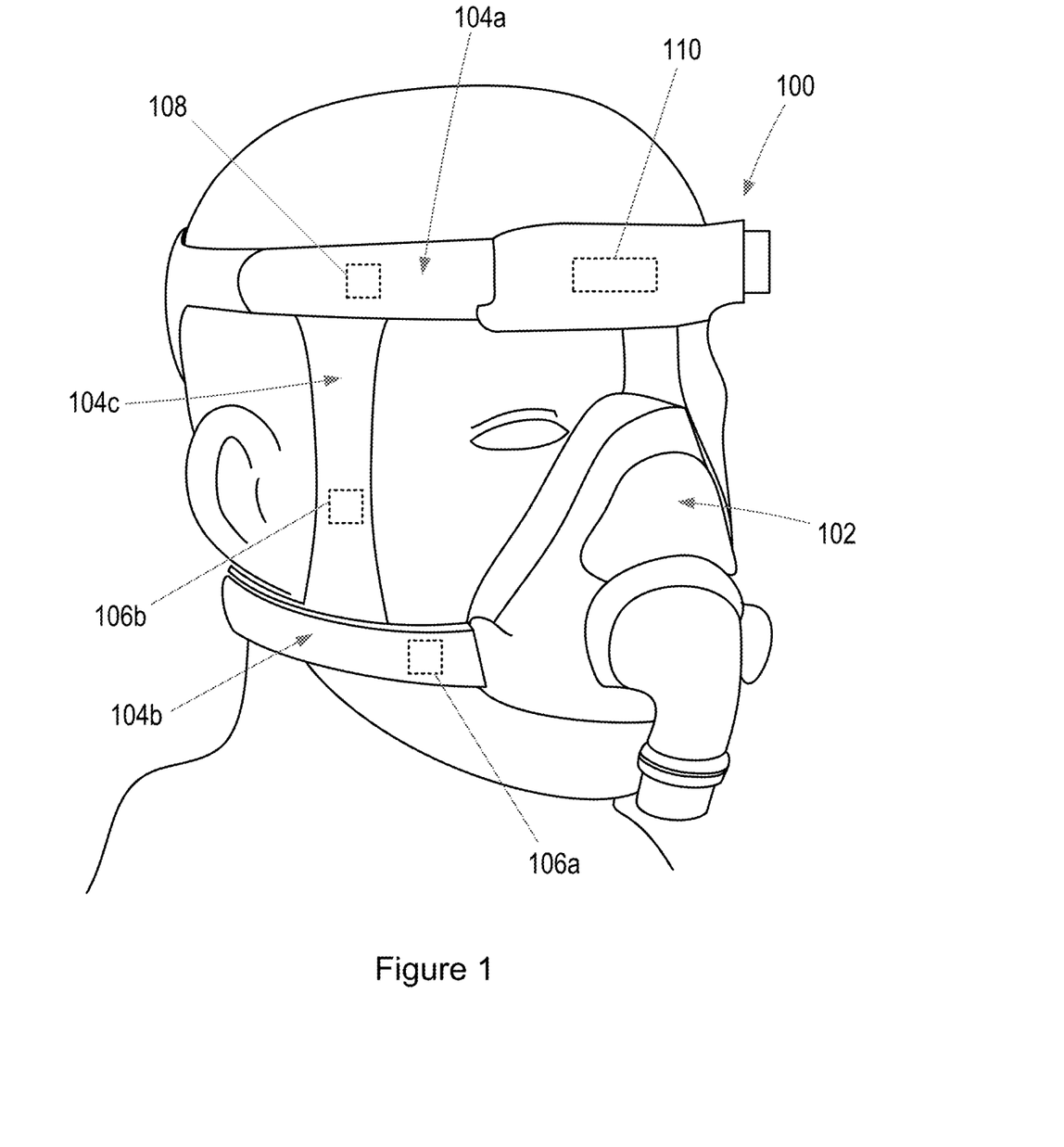
FIG. 1 is an illustration of a respiratory apparatus according to an embodiment.

FIG. 1 is an illustration of an example respiratory apparatus 100 according to an embodiment. The respiratory apparatus 100 comprises a respiratory interface (or respiratory mask) 102 configured to aid a user in respiration. According to this illustrated example embodiment, the respiratory interface (or the respiratory mask) 102 is configured to cover the mouth and the nose of the user to aid the user in respiration. However, it will be understood that other configurations for the respiratory interface 102 of the respiratory apparatus 100 are also possible. For example, in other embodiments, the respiratory interface 102 may be configured to cover only the mouth, only the nose, or the entire face of the user to aid the user in respiration.

The respiratory apparatus 100 also comprises an attachment. In the illustrated example embodiment of FIG. 1, the attachment comprises at least one strap 104a, 104b, 104c configured to hold the respiratory interface 102 in position on the face of the user. According to this illustrated example embodiment, the respiratory apparatus 100 comprises a first strap 104a configured for placement around the head of the user (at the forehead), a second strap 104b configured for placement around the head of the user (at the jaw), and a third strap 104c configured for placement between the first strap 104a and the second strap 104b.

However, it will be understood that other configurations for the at least one strap of the respiratory apparatus 100 are also possible. For example, in other embodiments, the respiratory apparatus may comprise the first strap 104a configured for placement around the head of the user (at the forehead) and the second strap 104b configured for placement around the head of the user (at the jaw), without the third strap 104c configured for placement between the first strap 104a and the second strap 104b. In any embodiment comprising more than one strap, at least two of the straps 104a, 104b, 104c may be formed from a single piece of material. Alternatively, one or more of the straps 104a, 104b, 104c may be formed from a separate (or extra) piece of material.

The respiratory apparatus 100 also comprises at least one electrode 106a, 106b configured to provide electrical stimulation to one or more facial muscles of the user. According to this illustrated example embodiment, the second strap 104b comprises at least one first electrode 106a and the third strap 104c comprises at least one second electrode 106b. However, it will be understood that other locations for the at least one electrode of the respiratory apparatus 100 are also possible. As mentioned earlier, the location for the at least one electrode can be any location where the at least one electrode can provide electrical stimulation to the one or more facial muscles of the user. In this illustrated example embodiment, the at least one first electrode 106a is located in the second strap 104b of the respiratory apparatus 100 to provide electrical stimulation to the zygomaticus major muscle and the at least one second electrode 106b is located in the third strap 104c of the respiratory apparatus 100 to provide electrical stimulation to the orbicularis oculi muscle.

Although not illustrated, the respiratory apparatus 100 on the left side of the face of the user may have the same configuration as that illustrated on the right side of the face of the user. For example, the respiratory apparatus 100 may comprise at least one pair of electrodes, with one of each pair located in corresponding straps on each side of the face of the user to provide electrical stimulation to corresponding muscles on each side of the face of the user.

In the illustrated example embodiment, the respiratory apparatus 100 further comprises at least one sleep stage sensor 108 configured to acquire a signal indicative of a sleep stage of the user. The first strap 104a of the respiratory apparatus 100 comprises the at least one sleep stage sensor 108 according to this illustrated example embodiment. However, it will be understood that other locations for the at least one sleep stage sensor 108 of the respiratory apparatus 100 are also possible. As mentioned earlier, the location for the at least one sleep stage sensor 108 can be any location where the at least one sleep stage sensor 108 can acquire a signal indicative of a sleep stage of the user.

In this illustrated example embodiment, the respiratory apparatus 100 also comprises a battery (or power supply) 110 for powering the respiratory apparatus 100. A part of the respiratory interface 102 at the forehead of the user comprises the battery 110 according to this illustrated example embodiment. However, it will be understood that other locations for the battery 110 of the respiratory apparatus 100 are also possible. For example, in other embodiments, at least one strap 104a, 104b, 104c of the respiratory apparatus 100 may comprise a battery 110. Although not illustrated in FIG. 1, the battery 110 may be electrically connected to the electrodes 106a, 106b and the sleep stage sensor 108 via one or more electrical wires.

Figure 2A:
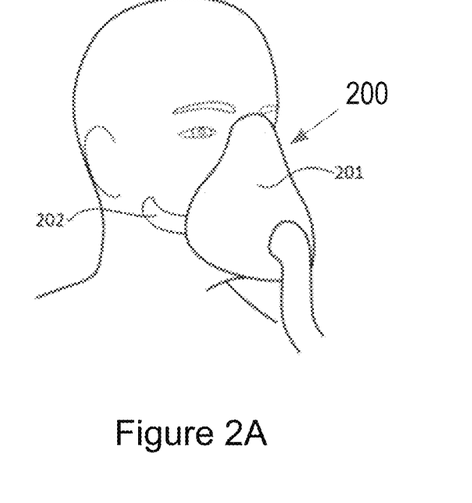
FIGS. 2A and 2B are illustrations of a respiratory apparatus according to another embodiment.
Figure 2B:
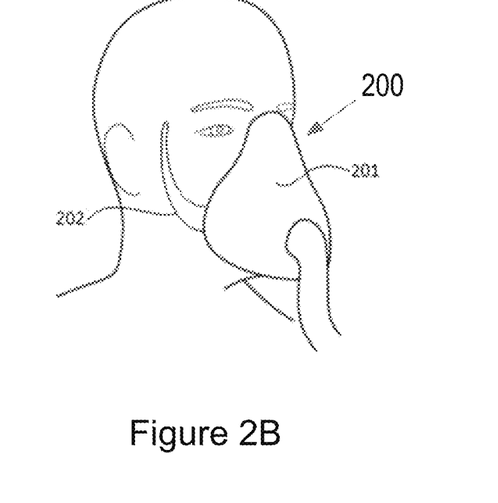

FIGS. 2A and 2B are illustrations of an example respiratory apparatus 200 according to another embodiment. The respiratory apparatus 200 comprises a respiratory interface (or respiratory mask) 201 configured to aid a user in respiration. According to this illustrated example embodiment, the respiratory interface (or the respiratory mask) 201 is configured to cover the mouth and the nose of the user to aid the user in respiration. However, it will be understood that other configurations for the respiratory interface 201 of the respiratory apparatus 200 are also possible. For example, in other embodiments, the respiratory interface 201 may be configured to cover only the mouth, only the nose, or the entire face of the user to aid the user in respiration.

The respiratory apparatus 200 also comprises an attachment. In the illustrated example embodiment of FIG. 2, the attachment comprises at least one adhesive member 202. The at least one adhesive member 202 can be structured to contact and adhere (for example, removeably bond) to the face of the user. For example, the at least one adhesive member 202 can comprise a contact surface and an adhesive layer provided on the contact surface. The adhesive layer can be arranged to contact and adhere (for example, removeably bond) to the face of the user. In some embodiments, the adhesive layer may be provided at, or on, certain portions of the contact surface. In other embodiments, the adhesive layer may be provided over the entire contact surface. The adhesive used for the adhesive layer can by any adhesive suitable to adhere (for example, removeably bond) to the face of the user. In some embodiments, the adhesive may be a medical-grade and/or biocompatible adhesive. Examples of adhesive that may be used include, but are not limited to, a silicone based adhesive, a polyurethane based adhesive, or any other adhesive, or any combination of adhesives suitable to adhere to the face of the user. However, it will be understood that other configurations for the at least one adhesive member 202 of the respiratory apparatus 200 are also possible.

The respiratory apparatus 200 also comprises at least one electrode configured to provide electrical stimulation to one or more facial muscles of the user. Although not illustrated, according to this example embodiment, the at least one adhesive member 202 may comprise at least one electrode. However, it will be understood that other locations for at least one electrode of the respiratory apparatus 200 are also possible. As mentioned earlier, the location for the at least one electrode can be any location where the at least one electrode can provide electrical stimulation to the one or more facial muscles of the user.

In the illustrated example embodiment of FIG. 2A, the at least one adhesive member 202 extends at least partially along the jaw of the user from the respiratory interface 201 at the corner of the mouth of the user such as at least partially along the zygomaticus major muscle. Thus, in the illustrated example embodiment of FIG. 2A, at least one first electrode may be located in the at least one adhesive member 202 of the respiratory apparatus 100 to provide electrical stimulation to the zygomaticus major muscle. In the illustrated example embodiment of FIG. 2B, the at least one adhesive member 202 extends upwardly toward a location between the ear and eye of the user from the respiratory interface 201 at the corner of the mouth of the user such as at least partially along the orbicularis oculi muscle. Thus, in the illustrated example embodiment of FIG. 2B, at least one first electrode may be located in the at least one adhesive member 202 of the respiratory apparatus 100 to provide electrical stimulation to the orbicularis oculi muscle.

Although not illustrated, the respiratory apparatus 200 on the left side of the face of the user may have the same configuration as that illustrated on the right side of the face of the user. For example, the respiratory apparatus 200 may comprise at least one pair of electrodes, with one of each pair located in corresponding adhesive members 202 on each side of the face of the user to provide electrical stimulation to corresponding muscles on each side of the face of the user.

Although not illustrated, the respiratory apparatus 200 may further comprise at least one sleep stage sensor configured to acquire a signal indicative of a sleep stage of the user. The at least one adhesive member 202 can comprise at least one sleep stage sensor. However, it will be understood that other locations for the at least one sleep stage sensor of the respiratory apparatus 200 are also possible. As mentioned earlier, the location for the at least one sleep stage sensor can be any location where the at least one sleep stage sensor can acquire a signal indicative of a sleep stage of the user.

Although not illustrated, the respiratory apparatus 200 can also comprise a battery (or power supply) for powering the respiratory apparatus 200. The battery may be electrically connected to the at least one electrode and any sleep stage sensors via one or more electrical wires.

Although examples have been provided according to the example embodiments illustrated in FIGS. 1, 2A and 2B for the configuration of the respiratory apparatus, it will be understood that other configurations are also possible. Similarly, although examples have been provided according to the example embodiments illustrated in FIGS. 1, 2 and 2A for the number, arrangement, and location of the attachment, the at least one electrode, the at least one sleep stage sensor, and the battery, it will be understood that other numbers, arrangements, and locations are also possible. Also, although not illustrated in FIGS. 1, 2A and 2B, the respiratory apparatus may further comprise at least one muscle contraction sensor.

As mentioned previously, a control unit (which may be a control unit of the respiratory apparatus or a control unit external to the apparatus) can be configured to control operation of the respiratory apparatus. In particular, as mentioned previously, the control unit may be configured to control the at least one electrode to provide the electrical stimulation to the one or more facial muscles of the user. The operation of the respiratory apparatus will now be described in more detail and will be understood to apply to any of the respiratory apparatus embodiments described herein.

In embodiments where the respiratory apparatus comprises at least one sleep stage sensor and/or where at least one sleep sensor is external to the respiratory apparatus, the control unit may be configured to control the at least one sleep sensor to acquire a signal indicative of a sleep stage of the user. The control unit may also be configured to control the at least one electrode to provide stimulation to the one or more facial muscles of the user based on the signal indicative of a sleep stage of the user that is acquired by the at least one sleep stage sensor. Thus, in some embodiments, the control unit may be configured to process the acquired signal to determine the sleep stage of the user.

In one embodiment, for example, the control unit may be configured to process the acquired signal to determine whether the user is sleeping. In these embodiments, the control unit can be configured to control the at least one electrode to provide electrical stimulation to the one or more facial muscles of the user when the acquired signal is indicative of the user sleeping. Thus, in some embodiments, the at least one electrode is controllable to provide electrical stimulation to the one or more facial muscles of the user when the acquired signal is indicative of the user sleeping. However, it will be understood that in other embodiments, the at least one electrode may alternatively be controllable to provide electrical stimulation to the one or more facial muscles of the user when the user is awake or irrespective of whether the user is sleeping or awake.

In another embodiment, for example, the control unit may be configured to process the acquired signal to determine a certain sleep stage of the user. In these embodiments, the control unit can be configured to control the at least one electrode to provide electrical stimulation to the one or more facial muscles of the user when the acquired signal is indicative of the user being in a certain sleep stage. For example, in some embodiments, the control unit can be configured to control the at least one electrode to provide electrical stimulation to the one or more facial muscles of the user when the acquired signal is indicative of the user being in a rapid eye movement sleep stage. Thus, in some embodiments, the at least one electrode is controllable to provide electrical stimulation to the one or more facial muscles of the user when the acquired signal is indicative of the user being in a rapid eye movement (REM) sleep stage. Once the acquired signal is indicative of the user being out of the rapid eye movement sleep stage (i.e. indicative of the user being in a non-rapid eye movement sleep stage), the control unit can be configured to control the at least one electrode to stop providing the electrical stimulation to the one or more facial muscles of the user. In some embodiments, this may be repeated during a plurality of sleep cycles of the user. Thus, in some embodiments, the one or more muscles are only stimulated during certain sleep stages of the user such as only during the rapid eye movement sleep stage of the user. In this way, power consumption can be reduced to thus increase battery life and the stimulation will be less disturbing for the user. This can be particularly important where the user has a sleep disorder such as sleep apnoea.

Although examples have been given for sleep stages in which electrical stimulation may be provided to the one or more facial muscles of the user, it will be understood that the at least one electrode may alternatively or in addition be controllable to provide electrical stimulation to the one or more facial muscles during other sleep stages.

In some embodiments, an intensity of the electrical stimulation may be based on the acquired signal indicative of a sleep stage of the user. For example, the control unit may be configured to process the acquired signal to determine an intensity for the electrical stimulation and to control the at least one electrode to provide electrical stimulation to the one or more facial muscles of the user at the determined intensity. For example, the control unit may be configured to control the at least one electrode to provide electrical stimulation to the one or more facial muscles of the user at a higher intensity when the acquired signal is indicative of the user being in a rapid eye movement sleep stage than when the acquired signal is indicative of the user being in a non-rapid eye movement sleep stage.

In embodiments where the respiratory apparatus comprises at least one muscle contraction sensor, the control unit may be configured to control the at least one muscle contraction sensor to detect one or more muscle contractions in the face of the user. The control unit may be configured to then control the at least one electrode to provide stimulation to the one or more facial muscles of the user based on the one or more muscle contractions in the face of the user detected by the at least one muscle contraction sensor. For example, in some embodiments, an intensity of the electrical stimulation may be based on the one or more muscle contractions detected in the face of the user.

In these embodiments, the control unit may be configured to process the one or more muscle contractions detected in the face of the user to determine an intensity for the electrical stimulation and to control the at least one electrode to provide electrical stimulation to the one or more facial muscles of the user at the determined intensity. This can allow for an improved control of the amount of power needed for the contraction. For example, the control unit may initially control the at least one electrode to provide low intensity electrical stimulation to the one or more facial muscles of the user and measure one or more facial muscle contractions. If the measured one or more facial muscle contractions are below a predefined threshold, the control unit may increase the intensity of the electrical stimulation provided to the one or more facial muscles and may continue to increase the intensity until a desired muscle contraction is reached. In this way, power consumption can be optimised to thus increase battery life and the stimulation can be less disturbing for the user. This can be particularly important where the user has a sleep disorder such as sleep apnoea.

In some embodiments, any one or more of the intensity and duration of the electrical stimulation provided by the at least one electrode can be set. For example, in some embodiments, the control unit may control the at least one electrode to increase (e.g. gradually increase) the intensity of the electrical stimulation provided to the one or more facial muscles of the user over a certain time period. Alternatively or in addition, the control unit may control the at least one electrode to provide electrical stimulation for a set time period (for example, over a period of 30 seconds, or any other time period). The intensity and/or the duration of the electrical stimulation provided by the at least one electrode may be adjustable by a user (for example, via the user interface). In this way, unpleasant sensations or pain in the face of the user can be prevented.

As mentioned earlier, the air tightness of the respiratory interface 102, 201 of the respiratory apparatus 100, 200 on the face of the user can be improved through the stimulation of one or more facial muscles of the user via the at least one electrode. Thus, the at least one pair of electrodes can be configured to provide electrical stimulation to one or more facial muscles of the user (as described herein) to improve the air tightness of (or reduce leaks in) the respiratory interface on the face of the user. In this respect, in some embodiments, the respiratory apparatus 102, 201 may further comprise an air pressure sensor configured to monitor an air pressure within the respiratory interface 102, 201. In this way, the air tightness of the respiratory interface 102, 201 on the face of the user can be determined since a change in the air pressure can be indicative of a change in the air tightness (such as an improved air tightness or a reduced air tightness, which may be due to a leak).

In embodiments in which the respiratory apparatus 100, 200 comprises a pump, the air pressure sensor may be the pump of the respiratory apparatus 100, 200. For example, the pump of the respiratory apparatus 100, 200 may be configured to detect a change in air pressure, which may be indicative of a leak in the respiratory interface 102, 201. Alternatively or in addition, in some embodiments, the respiratory interface 102, 201 of the apparatus 100, 200 may comprise an air pressure sensor (for example, an air pressure sensor may be integrated into the respiratory interface 102, 201). Examples of such an air pressure sensor include, but are not limited to, a piezoresistive sensor (such as a piezoresistive strain gauge), a capacitive sensor, an electromagnetic sensor, or any other air pressure sensor, or any combination of air pressure sensors.

In some embodiments, if the monitored air pressure is indicative of a leak in the respiratory interface 102, 201 on the face of the user, the at least one electrode may be controllable to adjust the electrical stimulation provided to the one or more facial muscles of the user. In some embodiments, the electrical stimulation may be adjusted until the monitored air pressure is indicative of the leak stopping. For example, the at least one electrode may be controllable to adjust the electrical stimulation provided to the one or more facial muscles of the user by switching on the electrical stimulation, switching off the electrode stimulation, or altering the intensity of the electrical stimulation. The control unit may be configured to control the at least one electrode in manner described.

In some embodiments, the respiratory apparatus 100, 200 may be configured to relieve pressure during exhalation of the user. In these embodiments, the control unit can be configured to control the at least one electrode to cease providing electrical stimulation to the one or more facial muscles of the user during exhalation of the user. Thus, the at least one electrode can be controllable to cease providing electrical stimulation to the one or more facial muscles of the user during exhalation of the user. The pressure relief can be provided due to the relaxation of the one or more facial muscles in the absence of the electrical stimulation (which can provide leakage in the respiratory interface 101, 201 of the apparatus 100, 200). This can also be useful to prevent strain on the one or more facial muscles of the user.

There is therefore provided an improved respiratory apparatus. The respiratory apparatus can be particularly useful for users of a respiratory apparatus that suffer from health issues such as sleep apnoea, depression, high blood pressure, and/or respiratory conditions. The respiratory apparatus can improve the wellbeing of the user such as by improving the mood of the user, reducing stress, and thus improving the general health of the user.

There is also provided a computer program product comprising a computer readable medium, the computer readable medium having computer readable code embodied therein, the computer readable code being configured such that, on execution by a suitable computer or processor, the computer or processor is caused to perform the method or methods described herein.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:
1. A respiratory apparatus comprising:
a respiratory interface configured to aid a user in respiration;
an attachment configured to hold the respiratory interface in position on the face of the user;
at least one electrode configured to provide electrical stimulation to one or more facial muscles of the user;
at least one sleep stage sensor configured to acquire a signal indicative of a sleep stage of the user, wherein the at least one electrode is controllable to provide electrical stimulation to the one or more facial muscles of the user when the acquired signal is indicative of the user sleeping;

an air pressure sensor configured to monitor an air pressure within the respiratory interface; and a control unit in communication with the at least one electrode and the air pressure sensor, wherein the control unit is programmed to adjust the electrical stimulation provided to the one or more facial muscles of the user if the monitored air pressure is indicative of a leak in the respiratory interface on the face of the user.

2. The respiratory apparatus of claim 1, wherein the attachment comprises at least one strap, or at least one adhesive member.

3. The respiratory apparatus of claim 1, wherein the attachment comprises the at least one electrode.

4. The respiratory apparatus of claim 1, wherein the at least one electrode comprises at least one pair of electrodes, the at least one pair of electrodes configured to provide electrical stimulation to corresponding muscles on each side of the face of the user.

5. The respiratory apparatus of claim 1, wherein the one or more facial muscles of the user comprise any one or more of:

a zygomaticus major muscle of the user; and
an orbicularis oculi muscle of the user.

6. The respiratory apparatus of claim 1, wherein the at least one sleep stage sensor comprises any one or more of:

a physiological characteristic sensor;
an eye movement sensor; and
an activity sensor.

7. The respiratory apparatus of claim 1, wherein the control unit is programmed to cause the at least one electrode to provide electrical stimulation to the one or more facial muscles of the user when the acquired signal is indicative of the user being in a rapid eye movement sleep stage.

8. The respiratory apparatus of claim 1, wherein an intensity of the electrical stimulation is based on the acquired signal indicative of a sleep stage of the user.

9. The respiratory apparatus of claim 1, wherein the respiratory apparatus further comprises:

at least one muscle contraction sensor configured to detect one or more muscle contractions in the face of the user.

10. The respiratory apparatus of claim 9, wherein an intensity of the electrical stimulation is based on the one or more muscle contractions detected in the face of the user.

11. The respiratory apparatus of claim 1, wherein the respiratory apparatus is a continuous positive airway pressure apparatus.

12. A method of operating the respiratory apparatus as claimed in claim 1, the method comprising:

controlling the at least one electrode to provide the electrical stimulation to the one or more facial muscles of the user.

13. The respiratory apparatus of claim 1, wherein the at least one electrode is positioned on the respiratory apparatus such that when the respiratory apparatus is positioned on the face of the user the at least one electrode is structured to provide electrical stimulation to any one or more of:

a zygomaticus major muscle of the user; and
an orbicularis oculi muscle of the user.

14. The respiratory apparatus of claim 1, wherein, if the monitored air pressure is indicative of a leak in the respiratory interface on the face of the user, the control unit is programmed to adjust the electrical stimulation provided to the one or more facial muscles of the user prior to the leak to a different intensity responsive to the leak.

15. The respiratory apparatus of claim 1, wherein the control unit is further programmed to:

control the at least one sleep stage sensor to acquire the signal indicative of the sleep stage of the user, and
control the at least one electrode to provide electrical stimulation to the one or more facial muscles of the user based on the signal indicative of a sleep stage of the user.

16. The respiratory apparatus of claim 1, wherein, if the monitored air pressure is indicative of a leak in the respiratory interface on the face of the user, the control unit is programmed to begin providing the electrical stimulation to the one or more facial muscles of the user responsive to the leak.

* * * * *